(12) United States Patent
Tayebi

(10) Patent No.: US 9,533,126 B1
(45) Date of Patent: Jan. 3, 2017

(54) APPARATUS FOR REINFORCING MEDICAL BALLOONS

(71) Applicant: Amad Tayebi, Westford, MA (US)

(72) Inventor: Amad Tayebi, Westford, MA (US)

( * ) Notice: Subject to any disclaimer, the term of this patent is extended or adjusted under 35 U.S.C. 154(b) by 0 days.

(21) Appl. No.: 14/756,110

(22) Filed: Aug. 3, 2015

Related U.S. Application Data

(63) Continuation-in-part of application No. 13/815,360, filed on Feb. 25, 2013, now Pat. No. 9,095,462, and a continuation-in-part of application No. 12/924,389, filed on Sep. 27, 2010, now Pat. No. 8,382,927, and a continuation-in-part of application No. 11/809,525, filed on Jun. 1, 2007, now Pat. No. 7,803,240.

(51) Int. Cl.
*A61M 25/10* (2013.01)
*A61F 2/958* (2013.01)

(52) U.S. Cl.
CPC .......... *A61M 25/1029* (2013.01); *A61F 2/958* (2013.01); *A61M 2025/1031* (2013.01); *A61M 2025/1075* (2013.01); *A61M 2025/1084* (2013.01); *A61M 2207/10* (2013.01)

(58) Field of Classification Search
CPC ................................................. A61M 25/1029
See application file for complete search history.

(56) References Cited

U.S. PATENT DOCUMENTS

| | | | | |
|---|---|---|---|---|
| 6,156,254 A | * | 12/2000 | Andrews | A61M 25/1029 264/231 |
| 2008/0183132 A1 | * | 7/2008 | Davies | A61M 25/104 604/103.09 |

* cited by examiner

*Primary Examiner* — Jeff Aftergut
(74) *Attorney, Agent, or Firm* — Amad Tayebi; American Patent Associates

(57) ABSTRACT

Disclosed is an apparatus for reinforcing medical balloons. The apparatus may be used for reinforcing any medical balloon by using a hollow tubular reinforcement sleeve. The sleeve may be in the form of a tubular braid, a tubular warp knitted fabric, a tubular weft knitted fabric or a tubular woven fabric. The apparatus may also be used for wrapping reinforcement yarns around the balloon.

9 Claims, 5 Drawing Sheets

US 9,533,126 B1

APPARATUS FOR REINFORCING MEDICAL BALLOONS

STATEMENT REGARDING RELATED APPLICATIONS

This Continuation-In-Part application claims priority of application Ser. No. 13/815,360 filed on Feb. 25, 2013 which is scheduled to issue on Aug. 4, 2015 as U.S. Pat. No. 9,095,462. This application incorporates, by reference, application Ser. No. 13/815,360, in its entirety.

Continuation-in-Part application Ser. No. 13/815,360 claims priority of application Ser. No. 12/924,389 filed on Sep. 27, 2010 (U.S. Pat. No. 8,382,927 issued on Feb. 26, 2013). This application incorporates, by reference, application Ser. No. 12/924,389, in its entirety.

Application Ser. No. 12/924,389 is a Continuation-in-Part of application Ser. No. 11/809,525 filed on Jun. 1, 2007 and issued on Sep. 28, 2010 as U.S. Pat. No. 7,803,240. This application incorporates, by reference, application Ser. No. 11/809,525, in its entirety.

Application Ser. No. 11/809,525 claimed priority of Provisional Application No. 60/809,941, filed on Jun. 1, 2006, and incorporated, by reference, said Provisional application in its entirety. This application incorporates, by reference, Provisional Application No. 60/809,941 in its entirety.

FIELD OF THE INVENTION

The present invention is in the field of medical balloons. In particular, it teaches and claims an apparatus for reinforcing medical balloons which are capable of withstanding high internal pressures without bursting. As such, the balloons, made in accordance with the present invention, are particularly suitable for use in balloon-tipped catheters where a collapsed wire stent is placed around the collapsed (deflated) balloon, the catheter is threaded through an artery to the location of the blockage. The balloon is then inflated in order to expand the stent surrounding it against the sides of the arterial wall. The balloon is then deflated, leaving the expanded stent in place against the artery wall and the catheter is removed.

BACKGROUND OF THE INVENTION

The prior art teaches and describes a variety of structures, methods and devices for making reinforced balloons for medical applications. Such structures, methods and devices are described in U.S. Pat. Nos. 4,490,421, Re. 33,561, Re. 32,983, 6,156,254, 5,201,706, 5,647,848, 4,706,670, 5,304,340, 5,554,120, 5,868,779, 6,746,425, 6,977,103, 6,190,358, 6,605,057, 6,210,364, 6,283,939 and 7,252,650 and pending U.S. patent applications, Pub. No.: US 2006/0224115, published on Oct. 5, 2006 and Pub. No.: US 2008/0183132, published on Jul. 31, 2008. Each of said U.S. patent and said pending patent applications is incorporated, by reference, in this application in its entirety.

The present invention provides a novel and simple apparatus for making reinforced balloons capable of withstanding high internal pressures. The method and the apparatus described may be used for reinforcing any medical balloon by using a hollow tubular reinforcement sleeve. The sleeve may be in the form of a tubular braid, a tubular knitted braid comprising warp yarns, a tubular warp knitted fabric, a tubular weft knitted fabric or a tubular woven fabric.

In accordance with open textile/fibrous structures literature and/or the present invention, jamming is a condition of high fabric packing density where a position of limiting structural geometry is reached due to the inability of solids to inter-penetrate during braid, knitted fabric (warp or weft knitted fabrics) or woven fabric formation and/or tensile, compressive and/or shear deformation. In the case of extensive jamming of a tubular braid or a tubular knitted sleeve (warp or weft knitted sleeve), it is the point where structural extension generated by the straightening and/or realignment of the fabric or braid threads in the direction of load stops and extension due to the straining of the strands/threads begins. For compressive jamming it is where strain from similar structural accommodation stops and buckling of the tubular braid or knitted sleeve starts. Also, in accordance with the present invention, the helix angle of a braid is the angle between the helix assumed by the braid element and the axis of the braid.

DESCRIPTION OF THE DRAWING ELEMENTS AND APPARATUS COMPONENTS

Figure 1:
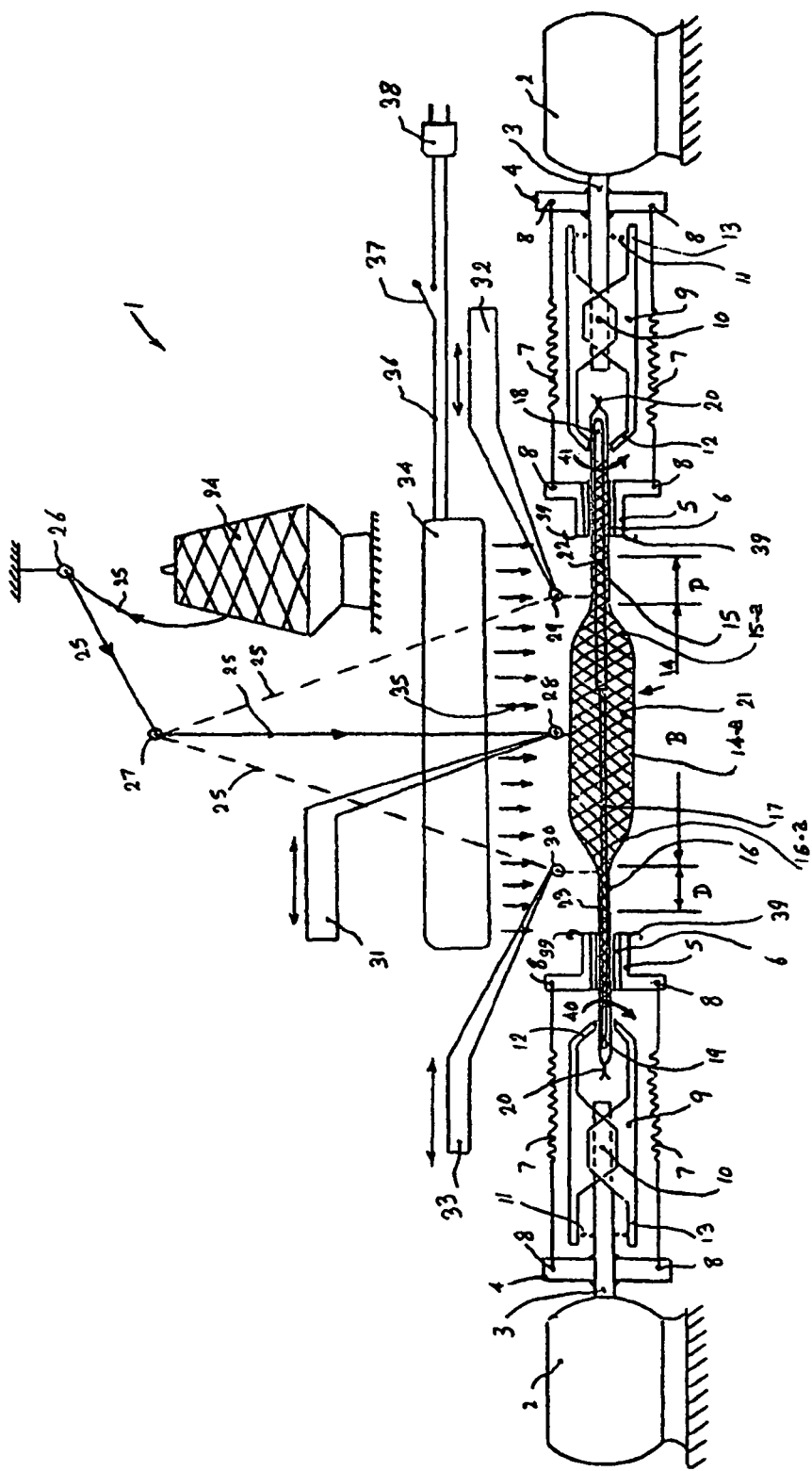
FIG. 1 is a longitudinal section view of the present invention apparatus used for reinforcing medical balloons.
Figure 2:
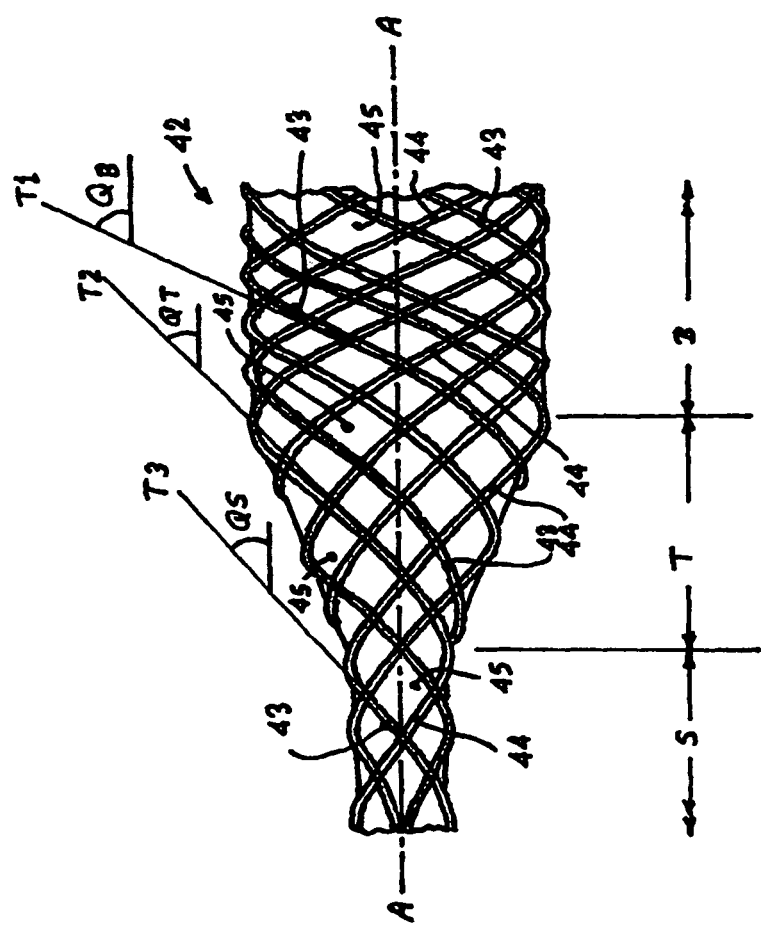
FIG. 2 shows a portion of a reinforced balloon, comprising a portion of balloon body, a transition zone and a portion of balloon shaft/neck, reinforced by using a hollow tubular reinforcement braid made of flat (un-textured) multi-filament reinforcement yarns.

FIG. 1 shows an embodiment of an apparatus designed, in accordance with the present invention, for performing the steps of a variety of processes of making reinforced medical balloons. Provided below is a description of the various elements shown in the drawings, (FIGS. 1, 2, 3, 4 and 5) and identified by their respective numbers:

1 Device for making reinforced balloons.

2 Sources of coaxial rotational motion for drive shafts 3. These two rotational motion sources may be separate but equal speed motors or two identical number of teeth gears receiving their drives from the same source, or other rotational motion drive sources known in the art. The directions of rotation of drive shafts 3, as viewed from a point located between them, are opposite to each other so that the balloon, as gripped by grippers 9, would rotate without experiencing any twisting action.

3 Drive shafts.

4 Spring ends anchoring/attaching blocks which are rigidly connected to drive shafts 3 and rotate with and at the same speed as drive shafts 3.

Figure 4:
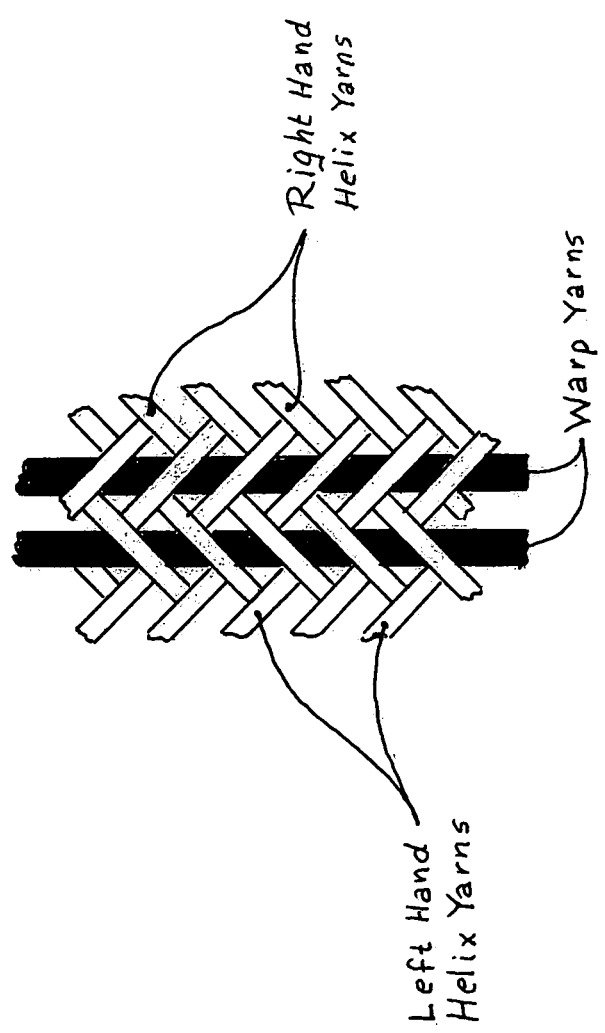
FIG. 4 shows a portion of a unified-layer/unified-multi-layer reinforcement braid comprising interlacing right hand helical path yarns, left hand helical path yarns and warp yarns held between the right hand and the left hand helical path yarns.

5 and 5A Reinforcement sleeve clamps. In an embodiment of the present invention, clamps 5 and 5A are in the form of radially-collapsible collars which clamp on the reinforcement sleeve (hollow braid or knitted tube) as they (the clamps) are pulled towards the spring ends anchoring blocks 4. Preferably, sleeve clamps 5 and 5A are lined with friction (anti slip) liners 6. Alternatively, clamps 5 and 5A may be substituted with hooks (not shown in the drawing) designed to engage with (hook onto) and axially stretch the ends of the reinforcement sleeve. The use of hooks to engage with and axially pull the ends of the reinforcement sleeve is particularly advantageous for the case of using reinforcement sleeves in the form of hollow tubular braids having warp yarns positioned between the right hand and the left hand helically-interlacing yarns, as shown in FIG. 4. In such a case, the use of hooks makes it possible to selectively engage with and axially pull the right hand and the left hand helically interlacing yarns while, in meantime, only straightening the warp yarns and maintaining their orientation parallel to the axis of the balloon and their positions (locations) equally spaced around the circumference of the reinforced balloon. In accordance with the present invention, the use of reinforcement braids comprising warp yarns, as shown in FIG. 4, and such hooks makes it possible to combine the right hand helical yarns, the left hand helical yarns and the warp yarns in a single unified layer that has a group of reinforcement yarns (the warp yarns) contributing their reinforcement force exclusively in the balloon axis direction and thus limiting/reducing the axial length growth (increase in length) of the reinforced balloon when the balloon is subjected to high internal pressure. In other words, the use of hooks makes it possible to ensure and maintain the axial direction of the warp yarns in a reinforcement braid comprising warp yarns. In an example of such a single unified layer comprising interlaced right hand helical-path yarns, left hand helical-path yarns and axially-oriented warp yarns, as shown in FIG. 4, a reinforcement braid for a 6 mm diameter balloon was made on a 64 carrier braider having 32 clockwise-rotating carriers, each carrying a flat (untextured) 70 denier, 34 filaments Nylon yarn, 32 counterclockwise-rotating carriers, each carrying flat (untextured) 70 denier, 34 filaments Nylon yarns and adapted to have 32 stationary hollow studs for guiding 32 warp yarns of the same Nylon yarn to be held between the clockwise-rotating yarns and the counterclockwise-rotating yarns, as shown in FIG. 4. Though unexpected and unplanned, the incorporation (interlacing) of the warp yarns in the above-described unified reinforcement braid resulted in a higher resistance of all of the braid yarns to shifting and thus produced a reinforcement braid with uniformly-spaced yarns and no excessive size open spacings between the braid yarns, especially in the transition zone connecting the balloon body to the conical transition zone. This is a very significant advantage since it increases the reinforced balloon resistance to abrasion because of the uniformity of surface coverage of the balloon surface with the reinforcement yarns.

Further, the incorporation of warp yarns, as discussed above, achieves in a single step what Beckham (U.S. Pat. No. 6,746,425) teaches and carries out in 3 separate and successive steps.

6 Reinforcement sleeve clamp friction/anti slip liners.
7 Tension springs stretching between anchoring blocks 4 and clamps 5/5A.

Alternatively, tension springs 7 may be substituted with elastomeric bands or other means known in the art to cause a pulling action on clamps 5 towards anchoring blocks 4.

8 End points of springs 7, shown in the extended state of springs 7.
9 and 9A Balloon end clamping grippers.
10 Fulcrums of Grippers 9/9A.
11 Springs acting on gripper handles/levers 13 to cause gripper clamping ends 12 to grip on balloon distal and proximal shafts and the optional mandrel ends within them.
12 Gripper clamping ends, normally in a closed (gripping) position under the action of springs 11.
13 Gripper handles/levers.
14 Balloon.
14-A Balloon body.
15 Balloon proximal/first shaft.
15-A Balloon proximal/first transition zone.
16 Balloon distal/second shaft.
16-A Balloon distal/second transition zone.
17 Mandrel (optional), having a diameter not larger than the inner diameter of the balloon distal shaft 16 and a length, as shown in FIG. 1, that is shorter than the end-to-end length of the balloon. The mandrel length, however, must be sufficient to enable grippers 9/9A to hold on portions of the balloon distal shaft and the balloon proximal shaft containing portions of mandrel 17. In another embodiment, mandrel 17 may have an end 19 having a diameter not larger than the inner diameter of the balloon distal shaft and another end 18 having a diameter larger than the inner diameter of the balloon distal shaft but not larger than the inner diameter of the balloon proximal shaft.
18 Large diameter end of mandrel 17.
19 Small diameter end of mandrel 17.
20/20A Hermetically sealed ends of pressurized balloon.
21 and 73 Reinforcement sleeve, shown for the case of a hollow round braid, in the balloon body portion, in the axially stretched and radially collapsed state.
22 Reinforcement sleeve, shown for the case of a hollow round braid, in the balloon proximal shaft zone, in the axially stretched and radially collapsed state.
23 Reinforcement sleeve, shown for the case of a hollow round braid, in the balloon distal shaft zone, in the axially stretched and radially collapsed state.
24 Yarn or high strength yarn (flat or textured) or thin narrow tape package/source.
25 Yarn or high strength yarn or thin narrow tape.
26 Stationery strand/yarn guide.
27 Stationary strand/yarn guide.
28 Traversing wrapping yarn guide covering zones D, B and P shown in FIGS. 1 and 5, which are the distal shaft zone, transitional and body zones and proximal shaft zone, respectively.
29 Traversing wrapping yarn guide covering the balloon proximal shaft zone, zone P.
30 Traversing wrapping yarn guide covering the balloon distal shaft zone, zone P.
31 Holder/actuator of guide 28.
32 Holder/actuator of guide 29.
33 Holder/actuator of guide 30.
34 Air heater and blower.
35 Hot air
36 Electrical wiring.
37 Electrical switch.
38 Electrical plug.
39 and 39A Hooks positioned around the circumference of clamps 5 and 5A, (optional). These hooks are adapted for holding yarns held by guide 28 as it (guide 28) traverses back and forth towards and behind hooks 39/39A to form longitudinal reinforcement elements stretching back and forth from the distal shaft zone to the proximal shaft zone.
40 Arrow showing direction of rotation of gripper 12 gripping distal end 16 of balloon.

41 Arrow showing direction of rotation of gripper 12 gripping proximal end 18 of balloon.
42 A portion of a reinforced balloon, comprising a portion of balloon body B, a transition zone T and a portion of balloon shaft S, reinforced by using a hollow tubular reinforcement braid (43 and 44) made of flat (un-textured) multi-filament reinforcement yarns 43 and 44.
43 Left hand yarn helices (S helices) of reinforcement braid.
44 Right hand yarn helices (Z helices) of reinforcement braid.
45 Open or uncovered zones of reinforced balloon between yarn helices.
T1 Tangent to reinforcement yarn helical path in the balloon body zone.
QB Helix angle of helical yarn path in the balloon body zone; angle between axis A-A (shown in FIG. 2) and tangent T1.
T2 Tangent to reinforcement yarn helical path in the balloon transition zone.
QT Helix angle of helical yarn path in the balloon transition zone; angle between axis A-A (shown in FIG. 2) and tangent T2.
T3 Tangent to reinforcement yarn helical path in the balloon shaft zone.
QS Helix angle of helical yarn path in the balloon shaft zone; angle between axis A-A (shown in FIG. 2) and tangent T3.
46 A portion of a reinforced balloon, comprising a portion of balloon body B, a transition zone T and a portion of balloon shaft S, reinforced by using a hollow tubular reinforcement braid (47 and 48) made of textured multi-filament reinforcement yarns 47 and 48.
47 Left hand yarn helices (S helices) of reinforcement braid.
48 Right hand yarn helices (Z helices) of reinforcement braid.
49 Open or uncovered zones of reinforced balloon between yarn helices.

SUMMARY OF THE CLAIMED INVENTION

Figure 5:
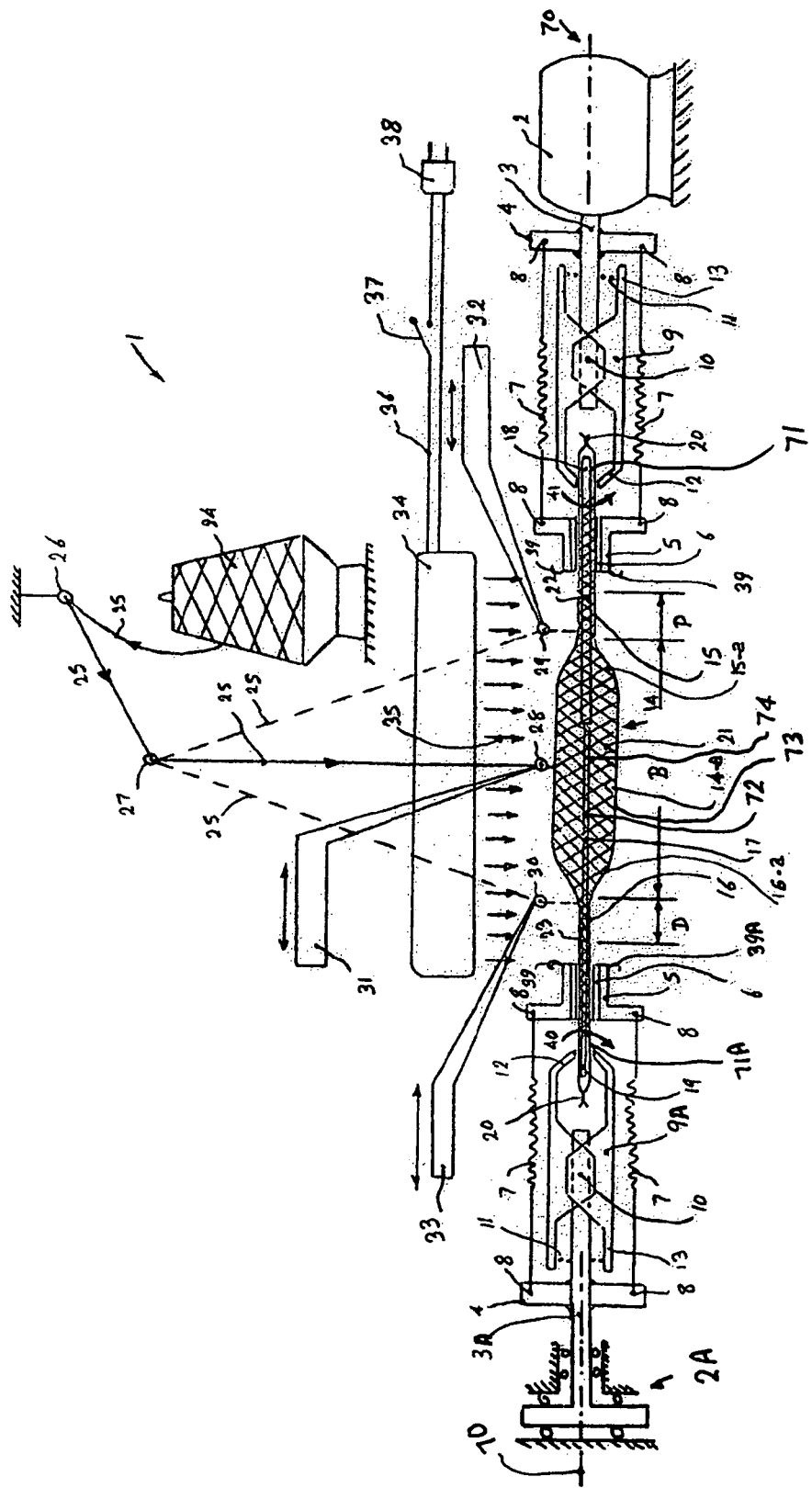
FIG. 5 shows a longitudinal section view of a variant of the apparatus shown in FIG. 1.

FIG. 5 shows an apparatus 1 for reinforcing a medical balloon 14. As shown therein and as described below, the apparatus comprises:

1) a first source of rotational motion 2 having an axis of rotation 70, said first source of rotational motion being adapted to a) have a first balloon end clamping gripper 9, said first gripper being attached to said first source of rotational motion 2 and being adapted to grip a first balloon shaft end 71 of a pressurized and hermetically-sealed medical balloon 14, said balloon having an axis 72, coinciding with said axis of rotation 70 of said first source of rotational motion 2, and comprising a balloon body 14A, a first balloon shaft 15, a first transitional zone 15A, a second balloon shaft 16, and a second transitional zone 16A, b) provide a rotational motion to said first gripper 9 around said axis of rotation 70, and c) have a first reinforcement sleeve clamp 5, said first reinforcement sleeve clamp being adapted to clamp a first end 22 of a reinforcement sleeve 73, said reinforcement sleeve having a first end 22 and a second end 23, and apply a tensile force, to said reinforcement sleeve, in a direction parallel to said axis of rotation 70 of said first source of rotational motion 2, said reinforcement sleeve 73 having an axis 74 parallel to said axis of rotation 70 of said first source of rotational motion 2 and covering said balloon body 14A, said first and second transitional zones 15A and 16A of said balloon 14, at least a portion of said first balloon shaft 15 and at least a portion of said second balloon shaft 16, 2) a supporting end 2A having a supporting end shaft 3A, said supporting end 2A being adapted to allow rotation of said supporting end shaft 3A around an axis, coinciding with said axis of rotation 70 of said first source of rotational motion 2, while not permitting said supporting end shaft 3A to have any substantial axial displacement, said supporting end shaft 3A being adapted to a) have a second balloon end clamping gripper 9A, said second gripper being attached to said supporting end shaft 3A and being adapted to grip a second balloon shaft end 71A of said pressurized and hermetically-sealed medical balloon 14, b) provide rotational motion to said second gripper 9A around said axis of rotation 70 of said first source of rotational motion 2, thereby enabling gripping a first balloon shaft end 71 and a second balloon shaft end 71A of a pressurized and hermetically-sealed balloon 14 and rotating said balloon around said axis of rotation 70 of said first source of rotational motion 2, and c) have a second reinforcement sleeve clamp 5A, said second reinforcement sleeve clamp being adapted to clamp said second end 23 of said reinforcement sleeve 73, and apply a tensile force, to said reinforcement sleeve, in a direction parallel to said axis of rotation 70 of said first source of rotational motion 2, thereby enabling clamping and application of a tensile force to said first end 22 and said second end 23 of said reinforcement sleeve 73, 3) at least one yarn-traversing actuator 31, 32 and/or 33, said actuator being adapted to a) have at least one yarn-traversing guide 28, 29 and/or 30, b) receive a lateral motion, from a lateral motion source, (not shown in the drawings) in a direction parallel to said axis of rotation 70 of said first source of rotational motion 2 and c) transmit said lateral motion to said at least one yarn-traversing guide, 4) at least one yarn package 24 positioned and oriented to allow unwinding of a yarn 25, 5) at least one yarn-path-guide 26 adapted to guide said yarn 25 to said at least one yarn-traversing guide 28, 29 and/or 30, thereby enabling wrapping a yarn a) around said first end 22 and said second end 23 of said reinforcement sleeve 73, and/or b) around said first balloon shaft 15, said first transitional zone 15A, said balloon body 14A, said second transitional zone 16A and said second balloon shaft 16, and 6) a hot air source and blower 34, adapted to provide a heated air stream onto said balloon 14, thereby enabling curing of an adhesive coating (not shown in the drawings) applied onto said reinforcement sleeve 73 and/or onto said yarn 25.

Optionally, apparatus 1 may also comprise a first set of equally spaced apart hooks 39 positioned on a circumference of said first reinforcement sleeve clamp 5 and a second set of equally spaced apart hooks 39A positioned on a circumference of said second reinforcement sleeve clamp 5A, said first set of hooks 39 and said second set of hooks 39A being adapted to hold segments of yarn 25 passing through said at least one yarn-traversing guide 28, 29 and/or 30, as said at least one yarn-traversing guide 28, 29, and/or 30 traverses back and forth, and forms yarn loops behind said first set of hooks 39 and behind said second set of hooks 39A, thereby forming equally spaced apart longitudinal (axial) reinforcement yarn segments, surrounding said balloon 14, stretching back and forth from said first balloon shaft 15 to said second balloon shaft 16 and being substantially parallel to said axis of rotation 70 of said first source of rotational motion 2.

Also, optionally, reinforcement sleeve 73 may be in the form of a hollow tubular braid comprising warp yarns. Further, yarn 25 may be a flat yarn, a textured yarn or, alternatively, a hybrid composite yarn.

DETAILED DESCRIPTION OF THE INVENTION

In accordance with the present invention, a method is provided for making a reinforced medical balloon, the method comprises the steps of providing a monolithic-structure balloon, said balloon comprising a balloon body, a proximal shaft, a distal shaft, a proximal transition zone and a distal transition zone, said balloon body having an outer diameter and a wall thickness, a proximal shaft outer diameter and a wall thickness and a distal shaft outer diameter and a wall thickness, providing a hollow tubular braid made of N reinforcement yarns, said braid being made on a tubular braiding machine utilizing a number of carriers N, a first half of said reinforcement yarns (N/2) forming right hand helices and a second half of said reinforcement yarns (N/2) forming left hand helices, said reinforcement yarns, of said first and said second halves, interlacing in accordance with a predetermined interlacing (weaving/braiding) pattern, said hollow tubular braid having a stress-free (i.e., as produced and laid on a flat surface under no externally applied load) inner diameter, a stress-free helix angle and an axial tension jammed state inner diameter and an axial compression-jammed state inner diameter, said axial compression-jammed state inner diameter being larger than said outer diameter of said balloon body and said tensile-jammed state inner diameter being not larger than said outer diameter of said distal shaft, said reinforcement yarns having a tensile breaking stress, a tensile modulus, and a slope/tangent of the initial portion of its stress-strain diagram defining the tangent of an angle, said balloon body having a hoop direction breaking stress and a hoop direction modulus and a slope/tangent of the initial portion of its stress-strain diagram defining the tangent of an angle, said balloon body having an axial direction breaking stress and an axial direction modulus and a slope/tangent of the initial portion of its stress-strain diagram defining the tangent of an angle, said tensile breaking stress of said reinforcement yarns being at least 4 gram per denier (68,567 psi for a polyester yarn) but preferably not exceeding 8 gram per denier (137,135 psi for a polyester yarn) and said tensile modulus of said reinforcement yarns being in the range of 50 to 95 gram per denier (857,091-1,628,471 psi for a polyester yarn) and said hoop direction tensile modulus of said balloon body being equal to said tensile modulus of said reinforcement yarns divided by r, where r is the ratio of said tensile modulus of said reinforcement yarns to said hoop direction tensile modulus of said balloon body, said ratio being at least equal to 4.0, sealing either the distal end or the proximal end of said balloon, inflating said balloon by introducing a pressurized fluid (gas or liquid) inside said balloon, thereby increasing its bending rigidity and resistance to lateral collapse, sealing the other end of said balloon, inserting said balloon inside said tubular braid, stretching said braid thereby causing it to collapse around said balloon, apply a radially-acting pressure on the exterior surface of the balloon and conform to the shape of said balloon, including said proximal shaft, said proximal transition zone, said balloon body, said distal transition zone and said distal shaft and forming a reinforcement yarn helix angle, in the zone of said body, in the range of 55 to 85 degrees, bonding said stretched braid to exterior surface of said balloon, deflating said balloon, and trimming/cutting said distal and proximal shafts to desired lengths.

Alternatively and in accordance with the present invention a method is provided for making a reinforced medical balloon, capable of withstanding high internal pressures without bursting and without excessive dilation. The method comprises the steps of;

providing a monolithic-structure balloon, said balloon comprising a balloon body, a proximal shaft, a distal shaft, a proximal transition zone and a distal transition zone, and a having an end-to-end balloon length, said balloon body having an outer diameter, an inner diameter and a wall thickness, said proximal shaft having a proximal shaft outer diameter, an inner diameter and a wall thickness and said distal shaft having a distal shaft outer diameter, an inner diameter and a wall thickness, providing a mandrel, said mandrel having a length shorter than said end-to-end balloon length and a diameter not exceeding the inner diameter of said distal shaft, hermetically sealing one end of said balloon, inserting said mandrel through the other end of said balloon, feeding a compressed fluid (gas or liquid) into said balloon through said other end of said balloon, hermetically sealing said other end of said balloon, thereby having a pressurized balloon containing a mandrel in its interior extending between said one end and said other end of said balloon, providing a hollow tubular reinforcement sleeve, said sleeve being a hollow tubular braid made of N reinforcement yarns, said braid being made on a tubular braiding machine utilizing a number of carriers N, a first half of said reinforcement yarns (N/2) forming right hand helices and a second half of said reinforcement yarns (N/2) forming left hand helices, said reinforcement yarns, of said first and said second halves, interlacing in accordance with a predetermined interlacing pattern, said hollow tubular braid having a stress-free inner diameter, and an axial tension-jammed state inner diameter and an axial compression-jammed state inner diameter, said axial compression-jammed state inner diameter being larger than said outer diameter of said balloon body, said reinforcement yarns having a tensile breaking stress, and a tensile modulus, said balloon body having a hoop direction breaking stress and a hoop direction modulus, said tensile breaking stress of said reinforcement yarns being at least 4 gram per denier (68,567 psi for a polyester yarn) but preferably not exceeding 8 gram per denier (137,135 psi for a polyester yarn) and said tensile modulus of said reinforcement yarns being in the range of 50 to 95 gram per denier (857,091-1,628,471 psi for a polyester yarn) and said hoop direction tensile modulus of said balloon body being equal to said tensile modulus of said reinforcement yarns divided by r, where r is the ratio of said tensile modulus of said reinforcement yarns to said hoop direction modulus of said balloon body, said ratio being at least equal to 4.0, inserting said balloon inside said tubular sleeve, providing a device comprising:

two spaced apart, first and second, coaxial drive shafts, said first and second coaxial drive shafts being rotatable at the same speed but opposite directions of rotation, as viewed from a point located between said first and second drive shafts, each of said drive shafts having i) a spring anchoring block rigidly attached to it and being connected to a reinforcement sleeve clamp by at least one tension spring extending between said anchoring block and said reinforcement sleeve clamp, and ii) a balloon end gripper rigidly attached to it and coaxially extending beyond the free end of each of said drive shafts, said gripper having a fulcrum, a release handle and a gripping end, said gripping end being normally closed under the action of a spring, at least one yarn guide located between said balloon end grippers, a yarn source and yarn guides that guide a yarn from said yarn source to said at least one yarn guide, and a source of hot air or radiant heat located in the area between said grippers, placing said balloon and reinforcement sleeve between said grippers and gripping the ends of said balloon containing said mandrel by said gripping ends of said grippers, using said reinforcement sleeve clamps, clamping and stretching said reinforcement sleeve thereby causing it to i) collapse around said balloon, ii) apply a radially-acting pressure on the exterior surface of said balloon and iii) conform to the shape of said balloon, including said proximal shaft, said proximal transition zone, said balloon body, said distal transition zone and said distal shaft and forming a reinforcement yarn helix angle, in the zone of said body of said balloon, in the range of 55 to 85 degrees, winding said yarn, from said yarn source, at least around said distal shaft and said proximal shaft of said balloon, by rotating said drive shafts and traversing said at least one yarn guide to cover said distal shaft and said proximal shaft with circumferential wrappings of said yarn from said yarn source, applying at least one coating of a bonding adhesive onto said balloon, said reinforcement sleeve and said circumferential wrappings to bond said balloon, said reinforcement sleeve and said circumferential wrappings and form a reinforced balloon, activating said source of hot air or radiant heat in order to cure said bonding adhesive, releasing said sleeve clamps and said grippers, removing said reinforced balloon, and cutting off the sealed ends of said balloon and removing said mandrel.

A major and unexpected difficulty encountered in carrying out the above steps of the above-described method of reinforcing balloons is that, during performing the step of stretching the reinforcement sleeve (braid); some of the braid yarns slip relative to one another (inter-yarn slippage), form irregular spaces between the yarns and leave large areas of the balloon surface uncovered and thus unreinforced. This is particularly the case when the reinforcement braid is made of flat (un-textured) multi-filament yarns due to the low inter-yarn coefficient of friction. It has also been noticed that this phenomenon occurs more frequently at the balloon shoulders (the areas connecting the transition zones to the balloon body). This may be attributed to the fact that the yarn helical length per helix pitch is longer in the balloon body area than in the transition zones, thus causing the yarns to slip from the body area to the transition zones in order to reduce their tension and strain energy.

It has also been observed that such inter-yarn slippage occurs randomly and thus results in a high variability (high standard deviation) in balloon bursting pressures. For example, a 6 millimeter diameter balloon having a wall thickness of 0.0006 inch reinforced by a 64 carrier braid made of a flat (un-textured) 70/34 (70 denier, 34 filaments) polyester yarn (one yarn per carrier) yielded bursting pressures averaging 30.2 atmospheres and ranging from 21 atmospheres to 41 atmospheres with a standard deviation of 4.3 atmospheres. This means that upon deducting three times the standard deviation from the average burst pressure, it is certain, with a probability of at least 99%, to have reinforced balloons, drawn from a large batch, with a bursting pressure of (30.2−[3×4.3])=17.3 atmospheres.

In contrast, when a 70/34 polyester multi-filament false twist textured yarn was used for making a 64 carrier reinforcement braid (one yarn per carrier) and used for reinforcing the same (6 millimeter diameter, 0.0006 inch wall thickness) balloon, the average burst pressure was 24.9 atmospheres and the standard deviation was 0.4 atmosphere. This means that upon deducting three times the standard deviation from the average burst pressure, it is certain, with a probability of at least 99%, to have reinforced balloons, drawn from a large batch, with a bursting pressure of (24.9−[3×0.4])=23.7 atmospheres.

In further contrast, when a 64 carrier reinforcement braid was made of hybrid/composite yarns, (one yarn per carrier), each yarn made of two parallel yarns, the first, a 70/34 nylon false-twist textured yarn and the second parallel yarn was made of a 70/34 un-textured flat yarn, the average bursting pressure was 29.5 atmospheres and the standard deviation was 0.8 atmosphere. This means that upon deducting three times the standard deviation from the average burst pressure, it is certain, with a probability of at least 99%, to have reinforced balloons, drawn from a large batch, with a bursting pressure of (29.5−[3×0.8])=27.1 atmospheres.

Figure 3:
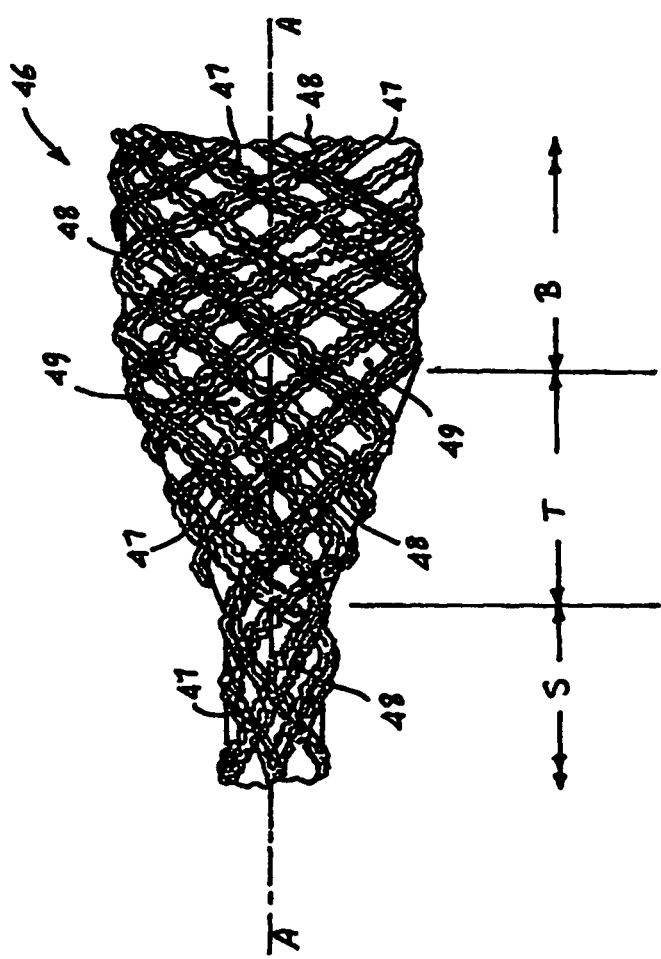
FIG. 3 shows a portion of a reinforced balloon, comprising a portion of balloon body, a transition zone and a portion of balloon shaft/neck, reinforced by using a hollow tubular reinforcement braid made of textured multi-filament reinforcement yarns.

Prior to experimenting with textured yarns, several attempts were made with un-textured (flat) yarns, adhesive-coated yarns, slit films, monofilaments and combinations thereof as strands to be used for making the reinforcement braids. None of these approaches yielded the consistent, yet unexpected results achieved by using textured yarns and hybrid/composite yarn combination such as the hybrid/composite yarn mentioned above. Based on the above data, it appears that the use of textured yarns yielded the unexpected result of reducing the inter-yarn slippage as well as reducing the size of the uncovered balloon surface areas (49) as depicted in FIG. 3. Further, and even more advantageous, the use of hybrid/composite yarns comprising a textured yarn and a flat yarn results in a higher bursting pressure and a consistently low variability (standard deviation) of burst pressure. This may be attributable to the increase of inter-yarn resistance to slippage attributable to the textured yarn and the reinforcement contribution obtained from the un-textured yarn.

In accordance with the present invention a textured multi-filament yarn is defined as a yarn comprising continuous filaments which, in their stress-free condition, follow other than straight paths. Such other than straight paths may be wavy, helical, zig-zag or any other non-straight line paths. An un-textured (flat) yarn is also accordingly defined as a yarn comprising filaments which, in their stress-free condition, follow straight line paths. Processes, known in the art, for making textutred yarns include false-twist texturing, stuffer box texturing, knit-deknit, gear crimping, . . . , etc.

A hybrid composite yarn is defined as a yarn made of at least two parallel yarns, one being a textured multi-filament yarn and the other being an untextured (flat) multi-filament yarn, monofilament or slit film.

The invention claimed is:

1. An apparatus for reinforcing a medical balloon, said apparatus comprising:
   1) a first and a second coaxial spaced apart drive shafts, said first and said second drive shafts being rotatable, around an axis of rotation, at the same speed but in opposite directions of rotation, as viewed from a point located between said first and said second drive shafts, each of said drive shafts having i) a free end, ii) a spring ends anchoring block rigidly attached to it, said anchoring block being connected to a reinforcement sleeve clamp by at least one tension spring, said tension spring extending between said anchoring block and said reinforcement sleeve clamp, and iii) a balloon end clamping gripper rigidly attached to it and coaxially extending beyond the free end of each of said drive shafts, said clamping gripper having a fulcrum, a release handle and a gripping end, said gripping end being normally closed under the action of a spring,
   said balloon end clamping gripper being adapted to grip an end of a balloon shaft of a pressurized and hermetically-sealed medical balloon, said balloon having an axis, coinciding with said axis of rotation and comprising a balloon body, a first balloon shaft, a first transitional zone, a second balloon shaft, and a second transitional zone,
   said reinforcement sleeve clamp being adapted to i) clamp an end of a reinforcement sleeve, said reinforcement sleeve having an axis coinciding with said axis of rotation and having a first end and a second end, and ii) apply a tensile force, to said reinforcement sleeve, in a direction parallel to said axis of rotation,
   said reinforcement sleeve covering said balloon body, said first and second transitional zones of said balloon, at least a portion of said first balloon shaft and at least a portion of said second balloon shaft,
   2) at least one yarn-traversing actuator, said actuator being adapted to i) have at least one yarn-traversing guide, ii)) receive a lateral motion, from a lateral motion source in a direction parallel to said axis of rotation and iii) transmit said lateral motion to said at least one yarn-traversing guide,
   3) at least one yarn package comprising a yarn and being positioned and oriented to allow unwinding of said yarn, and,
   4) at least one yarn-path-guide adapted to guide said yarn to said at least one yarn-traversing guide, thereby enabling wrapping a yarn a) around said first end and said second end of said reinforcement sleeve, and/or b) around said first balloon shaft, said first transitional zone, said balloon body, said second transitional zone and said second balloon shaft.

2. The apparatus of claim 1 further comprising a hot air source and blower, adapted to provide a heated air stream onto said balloon, thereby enabling curing of an adhesive coating applied onto said reinforcement sleeve and/or onto said yarn.

3. The apparatus of claim 1 further comprising a first set of equally spaced apart hooks positioned on a circumference of a first reinforcement sleeve clamp and a second set of equally spaced apart hooks positioned on a circumference of a second reinforcement sleeve clamp, said first set of hooks and said second set of hooks being adapted to hold segments of yarn passing through said at least one yarn-traversing guide, as said at least one yarn-traversing guide traverses back and forth and forms yarn loops behind said first set of hooks and behind said second set of hooks, thereby forming equally spaced apart longitudinal (axial) reinforcement yarn segments surrounding said balloon and extending back and forth from said first balloon shaft to said second balloon shaft and being substantially parallel to said axis of rotation.

4. The apparatus of claim 1 wherein said reinforcement sleeve being a hollow tubular braid.

5. The apparatus of claim 4 wherein said hollow tubular braid comprising warp yarns.

6. The apparatus of claim 1 wherein said reinforcement sleeve comprising a flat yarn.

7. The apparatus of claim 1 wherein said reinforcement sleeve comprising a textured yarn.

8. The apparatus of claim 1 wherein said reinforcement sleeve comprising a hybrid composite yarn.

9. The apparatus of claim 1 wherein said reinforcement sleeve being a hollow knitted sleeve.

* * * * *